US007815941B2

(12) United States Patent
Brown et al.

(10) Patent No.: US 7,815,941 B2
(45) Date of Patent: Oct. 19, 2010

(54) NUCLEIC ACID MICROSPHERES, PRODUCTION AND DELIVERY THEREOF

(75) Inventors: Larry R. Brown, Newton, MA (US); Terrence L. Scott, Winchester, MA (US); Debra Lafreniere, Dighton, MA (US); Vered Bisker-Leib, Woburn, MA (US)

(73) Assignees: Baxter Healthcare S.A., Glattpark (Opfikon) (CH); Baxter International Inc., Deerfield, IL (US)

( * ) Notice: Subject to any disclaimer, the term of this patent is extended or adjusted under 35 U.S.C. 154(b) by 0 days.

(21) Appl. No.: 11/127,362

(22) Filed: May 12, 2005

(65) Prior Publication Data

US 2006/0018971 A1   Jan. 26, 2006

Related U.S. Application Data

(60) Provisional application No. 60/570,273, filed on May 12, 2004, provisional application No. 60/625,311, filed on Nov. 5, 2004.

(51) Int. Cl.
*A61K 9/14* (2006.01)
*A61K 35/16* (2006.01)
*A01N 43/04* (2006.01)
(52) U.S. Cl. ............... 424/489; 514/44; 424/497
(58) Field of Classification Search ............... 424/489, 424/497; 514/44
See application file for complete search history.

(56) References Cited

U.S. PATENT DOCUMENTS

| | | |
|---|---|---|
| 3,737,337 A | 6/1973 | Schnoring et al. |
| 3,891,570 A | 6/1975 | Fukushima et al. |
| 4,389,330 A | 6/1983 | Tice et al. |
| 4,530,840 A | 7/1985 | Tice et al. |
| 4,584,894 A | 4/1986 | Fogelberg |
| 4,652,441 A | 3/1987 | Okada et al. |
| 4,728,721 A | 3/1988 | Yamamoto et al. |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum |
| 4,917,893 A | 4/1990 | Okada et al. |
| 5,075,109 A | 12/1991 | Tice et al. |
| 5,102,872 A | 4/1992 | Singh et al. |
| 5,149,543 A | 9/1992 | Cohen et al. |
| 5,213,812 A | 5/1993 | Ruiz |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Boyes et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,543,158 A | 8/1996 | Gref et al. |
| 5,556,642 A | 9/1996 | Kobayashi et al. |
| 5,575,987 A | 11/1996 | Kamei et al. |
| 5,578,709 A | 11/1996 | Woiszwillo |
| 5,599,719 A | 2/1997 | Woiszwillo |
| 5,603,961 A | 2/1997 | Suzuki et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A | 9/1997 | Cha et al. |
| 5,851,451 A | 12/1998 | Takechi et al. |
| 5,858,973 A | 1/1999 | Habener et al. |
| 5,932,248 A | 8/1999 | Chen et al. |
| 5,945,126 A | 8/1999 | Thanoo et al. |
| 5,972,707 A | 10/1999 | Roy et al. |
| 5,981,719 A | 11/1999 | Woiszwillo et al. |
| 5,989,463 A | 11/1999 | Tracy et al. |
| 5,994,314 A | 11/1999 | Eljamal et al. |
| 6,036,976 A | 3/2000 | Takechi et al. |
| 6,063,910 A | 5/2000 | Debenedetti et al. |
| 6,077,833 A | 6/2000 | Bennett et al. |

(Continued)

FOREIGN PATENT DOCUMENTS

CA      2157793 A1    9/1994

(Continued)

OTHER PUBLICATIONS

Ahn, C.H, et al., Biodegradable poly(ethylenimine) for plasmid DNA delivery, Journal of Controlled Release, 2002, vol. 80(1-3), pp. 273-282.

(Continued)

*Primary Examiner*—Fereydoun G Sajjadi
(74) *Attorney, Agent, or Firm*—Marshall, Gerstein & Borun LLP

(57) ABSTRACT

Nucleic acids are prepared by dissolving compounds containing them in a suitable solvent or solvent system and forming microspheres from the resulting solution. The microspheres are administered to an individual as protection from conditions where delivery of nucleic acids is useful, such as in treatment of autoimmune disease.

73 Claims, 8 Drawing Sheets

U.S. PATENT DOCUMENTS

| | | | |
|---|---|---|---|
| 6,090,925 | A | 7/2000 | Woiszwillo et al. |
| 6,120,787 | A | 9/2000 | Gustafsson et al. |
| 6,153,211 | A | 11/2000 | Hubbell et al. |
| 6,197,584 | B1 | 3/2001 | Bennett et al. |
| 6,252,055 | B1 | 6/2001 | Relton et al. |
| 6,265,389 | B1 | 7/2001 | Burke |
| 6,267,958 | B1 | 7/2001 | Andya et al. |
| 6,268,053 | B1 | 7/2001 | Woiszwillo et al. |
| 6,270,795 | B1 | 8/2001 | Jones et al. |
| 6,270,802 | B1 | 8/2001 | Thanoo et al. |
| 6,290,991 | B1 | 9/2001 | Roser et al. |
| 6,303,582 | B1 | 10/2001 | Eljamal et al. |
| 6,319,906 | B1 | 11/2001 | Bennett et al. |
| 6,361,798 | B1 | 3/2002 | Thanoo et al. |
| 6,395,253 | B2 | 5/2002 | Levy et al. |
| 6,395,302 | B1 | 5/2002 | Hennink et al. |
| 6,455,074 | B1 | 9/2002 | Tracy et al. |
| RE37,872 | E | 10/2002 | Franks et al. |
| 6,458,387 | B1* | 10/2002 | Scott et al. ............... 424/489 |
| 6,475,995 | B1 | 11/2002 | Roy et al. |
| 6,506,410 | B1 | 1/2003 | Park et al. |
| 6,534,483 | B1 | 3/2003 | Bruno et al. |
| 6,596,316 | B2 | 7/2003 | Lyons et al. |
| 6,616,949 | B2 | 9/2003 | Jonsson et al. |
| 6,630,169 | B1 | 10/2003 | Bot et al. |
| 6,645,525 | B1 | 11/2003 | Woiszwillo et al. |
| RE38,385 | E | 1/2004 | Franks et al. |
| 6,749,866 | B2 | 6/2004 | Bernstein et al. |
| 6,814,980 | B2 | 11/2004 | Levy et al. |
| 6,830,737 | B2 | 12/2004 | Ramstack |
| 6,849,259 | B2 | 2/2005 | Haurum et al. |
| 6,861,064 | B1 | 3/2005 | Laakso et al. |
| 6,875,432 | B2 | 4/2005 | Liu et al. |
| 7,129,222 | B2* | 10/2006 | Van Nest et al. ............ 514/44 |
| 2001/0002261 | A1 | 5/2001 | Morrison et al. |
| 2002/0009453 | A1 | 1/2002 | Haurum et al. |
| 2002/0045571 | A1 | 4/2002 | Liu et al. |
| 2002/0136719 | A1 | 9/2002 | Shenoy et al. |
| 2002/0146459 | A1 | 10/2002 | Levy et al. |
| 2002/0182258 | A1* | 12/2002 | Lunsford et al. ............ 424/499 |
| 2003/0007990 | A1 | 1/2003 | Blankenship et al. |
| 2003/0059474 | A1 | 3/2003 | Scott et al. |
| 2004/0014698 | A1 | 1/2004 | Hortelano et al. |
| 2004/0022081 | A1 | 2/2004 | Erickson et al. |
| 2004/0043076 | A1 | 3/2004 | Dulieu et al. |
| 2004/0185091 | A1 | 9/2004 | Truong et al. |
| 2004/0186071 | A1 | 9/2004 | Bennett et al. |
| 2004/0197324 | A1 | 10/2004 | Liu et al. |
| 2004/0219224 | A1 | 11/2004 | Yakovlevsky et al. |
| 2005/0053666 | A1 | 3/2005 | Tzannis et al. |
| 2005/0158303 | A1 | 7/2005 | Liu et al. |
| 2005/0175603 | A1 | 8/2005 | Liu et al. |
| 2005/0180967 | A1 | 8/2005 | Haurum et al. |
| 2005/0202072 | A1 | 9/2005 | Ruch-Rasmussen et al. |
| 2005/0271732 | A1 | 12/2005 | Suzuki et al. |
| 2006/0002862 | A1 | 1/2006 | Truong-Le et al. |
| 2006/0127395 | A1 | 6/2006 | Arvinte et al. |
| 2006/0182740 | A1 | 8/2006 | Yang et al. |
| 2006/0276425 | A1 | 12/2006 | Mourich et al. |
| 2007/0023776 | A1 | 2/2007 | Zakgeym et al. |
| 2007/0065440 | A1 | 3/2007 | Tomlinson et al. |
| 2007/0122411 | A1 | 5/2007 | Matheus et al. |
| 2007/0161589 | A1 | 7/2007 | Bennett et al. |
| 2007/0172475 | A1 | 7/2007 | Matheus et al. |
| 2007/0172479 | A1 | 7/2007 | Warne et al. |

FOREIGN PATENT DOCUMENTS

| | | |
|---|---|---|
| CA | 2157793 C | 9/1994 |
| EP | 248531 A2 | 1/1986 |
| EP | 248531 A3 | 1/1986 |
| EP | 0564061 B1 | 10/1993 |
| EP | 809110 A1 | 11/1997 |
| EP | 0936902 | 8/1999 |
| EP | 0957926 | 11/1999 |
| EP | 1060741 A1 | 12/2000 |
| EP | 1173151 B1 | 1/2002 |
| EP | 1173550 | 1/2002 |
| EP | 0975334 | 2/2002 |
| EP | 1283720 B1 | 2/2003 |
| EP | 1801123 A2 | 6/2004 |
| EP | 1614751 | 1/2006 |
| EP | 0907378 B1 | 2/2006 |
| JP | 2006219455 | 8/2006 |
| WO | WO 94/18947 | 9/1994 |
| WO | WO 94/20856 | 9/1994 |
| WO | WO-94/24263 | 10/1994 |
| WO | WO-96/03978 | 2/1996 |
| WO | WO-96/08289 | 3/1996 |
| WO | WO-97/45140 | 12/1997 |
| WO | WO 00/41679 A1 | 7/2000 |
| WO | WO-00/62759 | 10/2000 |
| WO | WO-01/89563 | 11/2001 |
| WO | WO-02/072636 | 9/2002 |
| WO | WO-02/096457 | 12/2002 |
| WO | WO 03/000014 A2 | 1/2003 |
| WO | WO-03/099228 | 12/2003 |
| WO | WO-2004/001007 | 12/2003 |
| WO | WO-2004/058156 | 7/2004 |
| WO | WO-2004/060343 | 7/2004 |
| WO | WO-2005/051355 | 6/2005 |
| WO | WO-2005/077414 | 8/2005 |
| WO | WO-2005/008443 | 9/2005 |
| WO | WO-2005/123131 | 12/2005 |
| WO | WO-2006/031560 | 3/2006 |
| WO | WO-2006/065746 | 6/2006 |
| WO | WO-2006/072527 | 7/2006 |
| WO | WO-2006/112838 | 10/2006 |
| WO | WO-2007/076062 | 7/2007 |

OTHER PUBLICATIONS

Banchereau and Steinman, Dendritic cells and the control of immunity, Nature, 1998, vol. 392, pp. 245-252.

Berton, M., et al., Improved oligonucleotide uptake and stability by a new drug carrier, the SupraMolecular BioVector (SMBV), Biochimica Biophysica Acta, 1997, vol. 1355, pp. 7-19.

Boussif, O. et al., A versatile vector for gene and oligonucleotide transfer into cells in culture and in vivo: Polyethylenimine, Proc. Natl. Acad. Sci. (U.S.A)., 1995, vol. 92, pp. 7297-7301.

Brazeau, G.A., et al., In vitro myotoxicity of selected cationic macromolecules used in non-viral gene delivery, Pharmaceutical Research, 1998, vol. 15(5), pp. 680-684.

Brown, et al., "Pulmonary Delivery of Novel Insulin Microspheres", Proceed, Respiratory Drug Delivery VIII, DHI Publishing, Raleigh, N.C., 2002, pp. 431-434.

Brown, et al., Promaxx Microsphere Characterization, in Proceed. Of Resp. Drug. Del. IX, 2004, pp. 477-479.

Bustami, et al., Generation of micro-particles of proteins for aerosol delivery using high pressure modified carbon dioxide, Pharmaceutical Research, Nov. 2000, vol. 17, No. 11, pp. 1360-1366.

Byrne and Halliday Dendritic cells: making progress with tumour regression? Immunology and Cell Biology, 2002, vol. 80, pp. 520-530.

Chamarthy, et al., A cationic peptide consists of ornithine and histidine repeats augments gene transfer in dendritic cells, Molecular. Immunology., 2003, vol. 40(8), pp. 483-490.

Check, E., A tragic setback, Nature, 2002, vol. 420, pp. 116-118.

Chollet, P., et al, Side-effects of a systemic injection of linear polyethylenimine-DNA complexes, Journal of Gene Medicine, 2002, vol. 4(1), pp. 84-91.

Chu, C.J., et al., Efficiency of cytoplasmic delivery by pH-sensitive liposomes to cells in culture, Pharm. Res., 1990, vol. 7, pp. 824-834.

Couvreur, P., et al., pH-sensitive liposomes: an intelligent design system for the delivery of antisense oligonucleotides. J. Liposome Res., 1997, vol. 7, pp. 1-18.

Crystal, R.G., Transfer of genes to humans: early lessons and obstacles for success, Science, 1995, vol. 270, pp. 404-410.

Dokka, S. et al., Inhibition of endotoxin-induced lung inflammation by interleukin-10 gene transfer in mice, Am J Physiol Lung Cell Mol Physiol, 2000, vol. 279(5), pp. L872-L877.

Felgner, P.L., et al., Cationic liposome-mediated transfection, 1989, Nature, vol. 337, pp. 387-388.

Glorioso, J.C., et al., Development of Herpes Simplex virus vectors for gene transfer to the central nervous system, in "Gene Therapeutics: Methods and Applications of Direct Gene Transfer", ed: Wolff, J., 1993, pp. 281-302.

Hudson, A.J., et al., Biodegradable polymer matrices for the sustained exogenous delivery of a biologically active c-myc hammerhead ribozyme, Int. J. Pharm., 1996, vol. 136, pp. 23-29.

Hughes, J.A., et al., Evaluation of adjuvants that enhance the effectiveness of antisense oligodeoxynucleotides. Pharm. Res., 1996, vol. 13, pp. 404-410.

Hwang, S.J., et al., Cationic polymers for gene delivery: designs for overcoming barriers to systemic administration, Curr. Opin. Mol. Ther., 2001, vol. 3, pp. 183-191.

Kabanov V.A., et al., Water-soluble block polycations as carriers for oligonucleotide delivery, Bioconjugate Chem., 1995, vol. 6, pp. 639-647.

Kataoka, K. et al., Spontaneous formation of polyion complex micelles with narrow distribution from antisense oligonucleotide and cationic block copolymer in physiological saline. Macromolecules. 1996. vol. 29. pp. 8556-8557.

Legendre, J.Y., Delivery of plasmid DNA into mammalian cell lines using pH-sensitive liposomes: comparison with cationic liposomes, Pharm. Res. 1992, vol. 9, pp. 1235-1242.

Loke, S.L. et al., Delivery of c-myc antisense phosphorothioate oligodeoxynucleotides to hematopoietic cells in culture by liposome fusion: specific reduction in c-myc protein expression correlates with inhibition of cell growth and DNA synthesis, Curr. Top. Microbiol. Immunol., 1988, vol. 141, pp. 282-289.

Mahato R.I., et al., Cationic lipid-based gene delivery systems: pharmaceutical perspectives, Pharm. Res., 1997, vol. 14, pp. 853-859.

Meiri N., et al., Reversible antisense inhibition of Shaker-like Kv1.1 potassium channel expression impairs associative memory in mouse and rat, Proc. Natl. Acad. Sci. U.S.A., 1997. vol. 94. pp. 4430-4434.

Middaugh, R.C., Oligonucleotide delivery, Encyclopedia of Controlled Drug Delivery, vol. 2, 1999, pp. 691-697.

Miller, A.D., Human gene therapy comes of age, Nature, 1992, vol. 357, pp. 455-460.

Moghimi, "Chemical camouflage of nanospheres with a poorly reactive surface: towards development of stealth and target-specific nanocarriers", Biochimica et Biophysica Acta, vol. 1590, pp. 131-139, 2000.

Morita, et al., Formation and Isolation of Spherical Fine Protein Microparticles Through Lyophilization of Protein-Poly (ethylene Glycol) Aqueous Mixture, Pharmaceutical Research, 2000, vol. 17, No. 11.

Oberhouser, B., et al., Enhancing endosomal exit of nucleic acids using pH-sensitive viral fusion peptides, In: Delivery Strategies for Antisense Oligonucleotides Therapeutics, Ed. Akhtar, S., 1995, pp. 247-266.

Perlaky, L., et al. Growth inhibition of human tumor cell lines by antisense oligonucleotides designed to inhibit p120 expression. Anti-Cancer Drug Des., 1993, vol. 8, pp. 3-14.

Radler, J.O., et al., Structure of DNA-cationic liposome complexes: DNA intercalation in multilamellar membranes in distinct interhelical packing regimes, Science, 1997, vol. 275, pp. 810-814.

Rashba-Step et al., Albumin Microspheres as Drug Delivery Vehicle for Multiple Routes of Administration, Proceed. Int'l. Symp. Control. Rel. Bioact. Materials., 2001, vol. 28.

Sah, H.K., et al.,Biodegradable microcapsules prepared by a w/o/w technique: effects of shear force to make a primary w/o emulsion on their morphology and protein release, J. of Microencapsulation, 1995, vol. 12(1), pp. 59-69.

Sinha, et al., Biodegradable microspheres for protein delivery, Journal of Controlled Release, 2003, vol. 90, pp. 261-280.

Sweeney et al, Efficient therapeutic gene delivery after systemic administration of a novel polyethylenimine/DNA vector in an orthotopic bladder cancer model.Cancer Res. Jul. 15, 2003, vol. 63, pp. 4017-4020.

Thierry, A.R., et al. Overcoming multidrug resistance in human tumor cells using free and liposomally encapsulated antisense oligodeoxynucleotides, Biochem. Biophys. Res. Commun., 1993, vol. 190, pp. 952-960.

Tiyaboonchai, W., et al., Formulation and characterization of DNA-polyethylenimine-dextran sulfate nanoparticles. European Journal of Pharmaceutical Sciences, Jul. 2003, vol. 19, pp. 191-202.

Tomlinson, E. et al., Controllable gene therapy Pharmaceutics of non-viral gene delivery systems J. Controlled Release, 1996, vol. 39, pp. 357-372.

Vanderkerken et al, Synthesis and evaluation of poly(ethylene glycol)-polylysine block copolymers as carriers for gene delivery, J. Bioactive and Compatible Polymers, 2000, vol. 15, pp. 115-138.

Yamakawa, I., et al., Release behavior of poly(lactic acid-co-glycolic acid) implants containing phosphorothioate oligodeoxynucleotide. Biol. Pharm. Bull, 1997, vol. 20, pp. 455-459.

Yang, et al., Crystalline monoclonal antibodies for subcutaneous delivery, Proc. Natl. Acad. Sci (USA), Jun. 10, 2003, vol. 100, No. 12, pp. 6934-6939.

Zhao, Q., et al., Modulation of oligonucleotide-induced immune stimulation by cyclodextrin analogs.Biochem. Pharmacol., 1996, vol. 52, pp. 1537-1544.

Report of the International Searching Authority PCT/US05/016660 pp. 1-3, Sep. 27, 2005.

Report of the International Searching Authority PCT/US05/16689 pp. 1-5, Nov. 29, 2005.

Opinion of the International Searching Authority PCT/US05/016660 pp. 1-7, Sep. 27, 2005.

Opinion of the International Searching Authority PCT/US05/16689 pp. 1-3, Nov. 29, 2005.

European Patent Office Search Report for EP05748256.4, dated May 8, 2007.

US 5,849,884, 12/1998, Woiszwillo et al. (withdrawn)

* cited by examiner

SEM 0.2-1.4μm

SEQUENCE LISTING

```
<160> NUMBER OF SEQ ID NOS: 5

<210> SEQ ID NO 1
<211> LENGTH: 31
<212> TYPE: DNA
<213> ORGANISM: Mus musculus

<400> SEQUENCE: 1
cacagccgag gcaaagacac catgcagggc a                           31

<210> SEQ ID NO 2
<211> LENGTH: 29
<212> TYPE: DNA
<213> ORGANISM: Mus musculus

<400> SEQUENCE: 2
gggaaagcca ggaatctaga gccaatgga                              29

<210> SEQ ID NO 3
<211> LENGTH: 30
<212> TYPE: DNA
<213> ORGANISM: Mus  Musculus

<400> SEQUENCE: 3
tgggtgcttc cgtaagttct ggaacacgtc                             30

<210> SEQ ID NO 4
<211> LENGTH: 21
<212> TYPE: RNA
<213> ORGANISM: Mus musculus

<400> SEQUENCE: 4
```

```
ggaaagacug uuccaaaaau u                                              21
```

<210> SEQ ID NO 5
<211> LENGTH: 21
<212> TYPE: RNA
<213> ORGANISM: Mus musculus

<400> SEQUENCE: 5

```
uuuuuggaac agucuuuccu u                                              21
```

NUCLEIC ACID MICROSPHERES, PRODUCTION AND DELIVERY THEREOF

CROSS REFERENCE TO RELATED APPLICATIONS

This claims priority of Provisional Patent Application Ser. No. 60/570,273 filed May 12, 2004 and Provisional Patent Application Ser. No. 60/625,311 filed Nov. 5, 2004.

FIELD OF THE INVENTION

The present invention generally relates to preparation of nucleic acid microspheres and their delivery, particularly in order to induce dendritic cell tolerance in addressing medical issues. More particularly, the invention relates to drug delivery technology by way of microspheres that are fabricated using aqueous conditions. The microspheres can incorporate interfering RNA, plasmid DNA, antisense (AS) oligonucleotides or other nucleic acids. These microspheres are used for alteration of cell function in vivo and in situ.

BACKGROUND OF THE INVENTION

Microparticles, microspheres, and microcapsules are solid or semi-solid particles having a diameter of less than one millimeter, more preferably less than 100 microns, which can be formed of a variety of materials, including synthetic polymers, proteins, and polysaccharides. Microspheres have been used in many different applications, primarily separations, diagnostics, and drug delivery.

A number of different techniques can be used to make these microspheres from synthetic polymers, natural polymers, proteins and polysaccharides, including phase separation, solvent evaporation, emulsification, and spray drying. Generally, the polymers form the supporting structure of these microspheres, and the drug of interest is incorporated into the polymer structure. Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., U.S. Pat. No. 5,384,133 to Boyes et al., U.S. Pat. No. 5,360,610 to Tice et al., and European Patent Application Publication Number 248,531 to Southern Research Institute; block copolymers such as tetronic 908 and poloxamer 407 as described in U.S. Pat. No. 4,904,479 to Illum; and polyphosphazenes as described in U.S. Pat. No. 5,149,543 to Cohen et al. Microspheres produced using polymers such as these exhibit a poor loading efficiency and are often only able to incorporate a small percentage of the drug of interest into the polymer structure. Therefore, substantial quantities of microspheres often must be administered to achieve a therapeutic effect.

Spherical beads or particles have been commercially available as a tool for biochemists for many years. For example, antibodies conjugated to beads create relatively large particles specific for particular ligands. The large antibody-coated particles are routinely used to crosslink receptors on the surface of a cell for cellular activation, are bound to a solid phase for immunoaffinity purification, and may be used to deliver a therapeutic agent that is slowly released over time, using tissue or tumor-specific antibodies conjugated to the particles to target the agent to the desired site.

A common method of covalently binding an antibody to a solid phase matrix is to derivatize a bead with a chemical conjugating agent and then bind the antibody to the activated bead. The use of a synthetic polymeric bead rather than a protein molecule allows the use of much harsher derivatization conditions than many proteins can sustain, is relatively inexpensive, and often yields a linkage that is stable to a wide range of denaturing conditions. A number of derivatized beads are commercially available, all with various constituents and sizes. Beads formed from synthetic polymers such as polyacrylamide, polyacrylate, polystyrene, or latex are commercially available from numerous sources such as Bio-Rad Laboratories (Richmond, Calif.) and LKB Produkter (Stockholm, Sweden). Beads formed from natural macromolecules and particles such as agarose, crosslinked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia. Magnetic beads are commercially available from sources such as Dynal Inc. (Great Neck, N.Y.).

One disadvantage of the microparticles or beads currently available is that they are difficult and expensive to produce. Microparticles produced by these known methods have a wide particle size distribution, often lack uniformity, and fail to exhibit long term release kinetics when the concentration of active ingredients is high. Furthermore, the polymers used in these known methods are dissolved in organic solvents in order to form the microparticles. They must therefore be produced in special facilities designed to handle organic solvents. These organic solvents could denature proteins or peptides contained in the microparticles. Residual organic solvents could be toxic when administered to humans or animals.

In addition, the available microparticles are rarely of a size sufficiently small to fit through the aperture of the size of needle commonly used to administer therapeutics or to be useful for administration by inhalation. For example, microparticles prepared using polylactic glycolic acid (PLGA) are large and have a tendency to aggregate. A size selection step, resulting in product loss, is necessary to remove particles too large for injection. PLGA particles that are of a suitable size for injection must be administered through a large gauge needle to accommodate the large particle size, often causing discomfort for the patient.

Generally, many currently available microparticles are activated to release their contents in aqueous media and therefore must be lyophilized to prevent premature release. In addition, particles such as those prepared using the PLGA system exhibit release kinetics based on both erosion and diffusion. In this type of system, an initial burst or rapid release of drug is observed. This burst effect can result in unwanted side effects in patients to whom the particles have been administered.

Microparticles prepared using lipids to encapsulate target drugs are known. For example, lipids arranged in bilayer membranes surrounding multiple aqueous compartments to form particles may be used to encapsulate water soluble drugs for subsequent delivery, as described in U.S. Pat. No. 5,422,120 to Sinil Kim. These particles are generally greater than 10 microns in size and are designed for intra-articular, intrathecal, subcutaneous and epidural administration. Alternatively, liposomes have been used for intravenous delivery of small molecules. Liposomes are spherical particles composed of a single or multiple phospholipid and cholesterol bilayers. Liposomes are 30 microns or greater in size and may carry a variety of water-soluble or lipid-soluble drugs. Liposome technology has been hindered by problems including purity of lipid components, possible toxicity, vesicle heterogeneity and stability, excessive uptake and manufacturing or shelf-life difficulties.

An objective for the medical community is the delivery of nucleic acids to the cells in a subject, including but not limited to an animal or a mammal, for treatment. For example, nucleic acids can be delivered to cells in culture (in vitro) relatively efficiently, but nucleases result in a high rate of nucleic acid degradation when nucleic acid is delivered to animals (in vivo).

In addition to protecting nucleic acid from nuclease digestion, a nucleic acid delivery vehicle must exhibit low toxicity, must be efficiently taken up by cells and have a well-defined, readily manufactured formulation. As shown in clinical trials, viral vectors for delivery can result in a severely adverse, even fatal, immune response in vivo. In addition, this method has the potential to have mutagenic effects in vivo. Delivery by enclosing nucleic acid in lipid complexes of different formulations (such as liposomes or cationic lipid complexes) has been generally ineffective in vivo and can have toxic effects. Complexes of nucleic acids with various polymers or with peptides have shown inconsistent results and the toxicity of these formulations has not yet been resolved. Nucleic acids have also been encapsulated in polymer matrices for delivery but in these cases the particles have a wide size range and the effectiveness for therapeutic applications has not been demonstrated.

Therefore, there is a need for addressing nucleic acid delivery issues, and providing effective nucleic acid formulations. Also, there is an ongoing need for development of microspheres and to new methods for making microspheres. Microspheres and their preparation have been described in U.S. Pat. No. 6,458,387 to Scott et al., No. 6,268,053, No. 6,090,925, No. 5,981,719 and No. 5,599,719 to Woiszwillo et al., and No. 5,578,709 to Woiszwillo. The foregoing references and all other references identified herein are incorporated herein by reference.

SUMMARY OF THE INVENTION

The present invention is directed to microspheres comprised of biologically active agents, such as DNA, siRNA (silencing RNA, also known as double-stranded RNA), mRNA, tRNA, and all other nucleic acids including, but not limited to, oligonucleotides, and to methods of preparation and use thereof. It is believed that the present invention microsphere delivery approach prevents or impedes access of the delivered nucleic acids to cellular nucleases, thereby preventing premature degradation of the therapeutic nucleic acids.

The nucleic acid containing microspheres can be used for the treatment of various diseases, including, but not limited to, autoimmune diseases such as multiple sclerosis, diabetes mellitus type 1, psoriasis, autoimmune hemolytic anemia, autoimmune hepatitis, Berger's disease (IgA nephropathy), chronic fatigue syndrome, Crohn's disease, dermatomyostis, fibromyalgia, Grave's disease, Hashimoto's thyroiditis, lichen planus, myasthenia gravis, odopathic thrombocytopenia purpura, rheumatic fever, rheumatoid arthritis, scleroderma, Sjogren syndrome, systemic lupus erythematosus, ulcerative colitis and vitiligo. Furthermore, the microspheres can be used to treat other dendritic cell or macrophage related diseases or other phagocytic cell-based diseases or conditions including those which can be treated, mediated or mitigated by antisense oligonucleotide or siRNA approaches, or the like.

In an embodiment of the invention, microsphere delivery of AS-oligonucleotides to a subject is carried out in order to induce dendritic cell tolerance in conjunction with addressing type 1 diabetes onset in individuals. The AS oligonucleotide containing microspheres are fabricated using aqueous conditions. These microspheres are used to inhibit gene expression and to prevent an autoimmune diabetes type of condition in a subject. Microspheres of the present invention can be used to treat ongoing conditions or as preventative therapy.

The microspheres of the present invention may also be comprised of multiple biologically active agents, including oligonucleotides.

In a preferred embodiment of the invention, three AS-oligonucleotides targeted to the CD40, CD80 and CD86 primary transcripts are synthesized, and an aqueous solution of the oligonucleotide mixture is prepared and combined with a polymer solution. After processing, microspheres containing the oligonucleotides are provided.

Preparation of the present invention microspheres can be carried out with or without a cross-linking agent, a polycation, a polyanion, and/or an energy source such as heat.

The microspheres according to the invention are especially well-suited to be administered in vivo and in an in situ procedure, such as direct subcutaneous delivery. One application in this regard is for the treatment of tumors under the skin and for treatment of viral infection. The microspheres can be delivered through a variety of other routes of administration including, but not limited to, oral, pulmonary, nasal, intravenous, intramuscular, subcutaneous, topical, ocular, intradermal, intraperitoneal, and suppository administration, and combinations thereof.

The microspheres of the present invention can also be used for diagnostic purposes, including, but not limited to, gene diagnostics.

These and other aspects, objects, features and advantages of the present invention, including the various combinations, will be apparent from and clearly understood through a consideration of the following detailed description.

BRIEF DESCRIPTION OF THE DRAWINGS

In the course of this description, reference will be made to the attached drawings, wherein.

DESCRIPTION OF THE PREFERRED EMBODIMENTS

Figure 1:
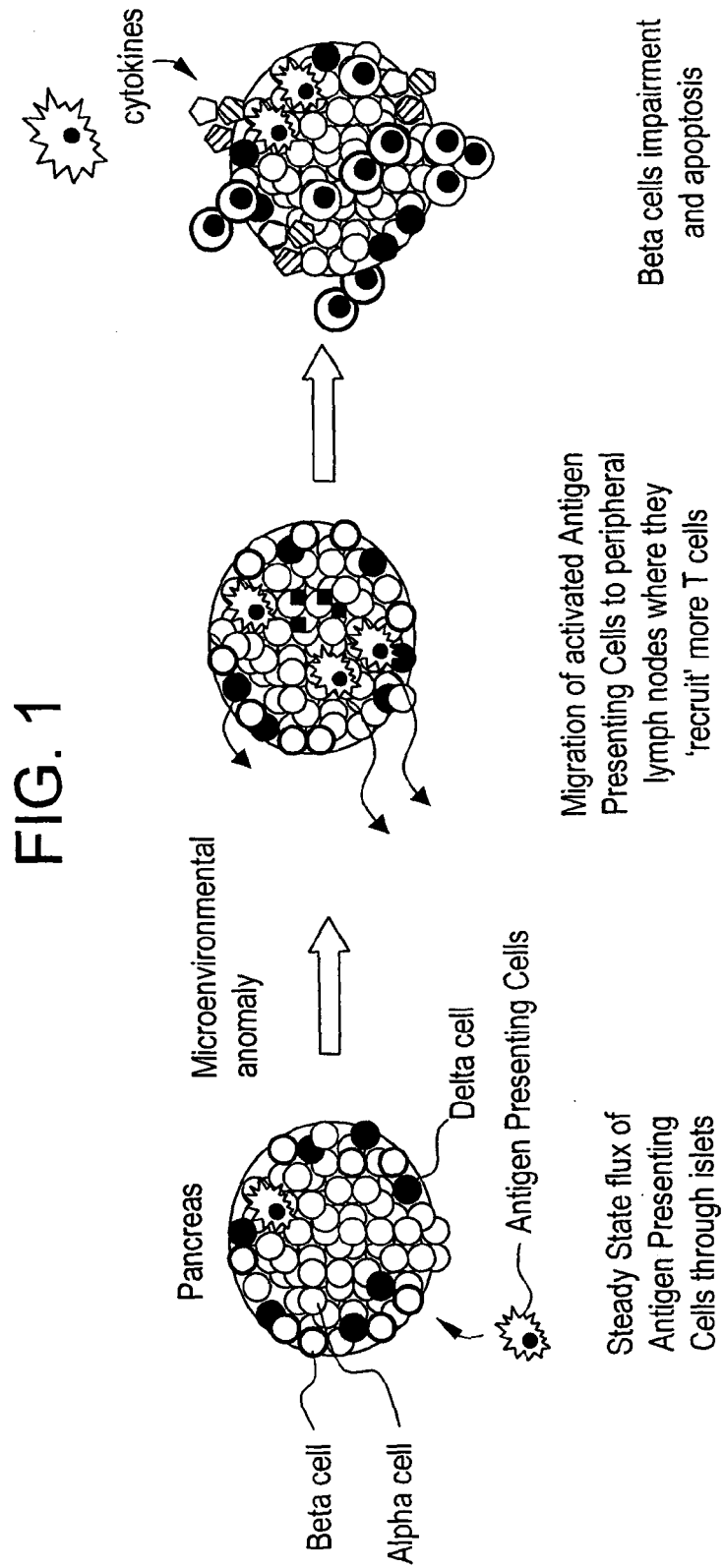
FIG. 1 is a schematic illustration of the role of dendritic cells in the autoimmune destruction of pancreatic insulin-producing beta-cells in Type 1 diabetes.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

In general, microspheres of the present invention are comprised of an active agent or agents, are preferably substantially spherical, and have a substantially narrow size distribution in the size range suitable for cell uptake. The microspheres can be delivered by administration methods of choice, including parenteral delivery, by the oral route, by the pulmonary route, by the ocular route, by using a depot system, and other administration routes.

The microspheres comprise nucleic acid active agents such as DNA, RNA, siRNA, mRNA, tRNA and other types of nucleic acids including, but not limited to, RNA or DNA oligonucleotides, and combinations thereof. Preferred microspheres of the present invention are comprised of one or more oligonucleotides. The microspheres are useful as therapeutic agents for the treatment of various diseases and/or as tools for diagnostic work, including, but not limited to, functional genomics. For example, antisense oligonucleotides microspheres can interrupt the translation phase of the protein production process by preventing the mRNA from reaching the ribosome. The antisense microspheres are delivered to the diseased cell, virus or bacteria, where they bind (hybridize) specifically to its target mRNA. As a result, the mRNA is degraded and therefore is not translated by the ribosome to a functional protein. Antisense microspheres are thus an effective tool to fight illness related to overexpression and/or underexpression of proteins in the body, such as occurs in autoimmune diseases.

Important advantages of antisense oligonucleotides are that they are highly specific in that they inhibit the expression of one gene. Also, antisense oligonucleotides are universal in that theoretically an AS oligonucleotide can be developed against any gene and its mRNA; the DNA sequence is the only information needed for the design of the AS nucleotide. AS oligonucleotides are also effective in the cultured cells of animals and humans. Antisense oligonucleotide microspheres of the present invention are also "verifiable," in that they are diagnostically useful because they have very specific sites and can be labeled with a fluorescent marker.

It is known that oligonucleotides are readily damaged by heat, shaking and other mechanical and chemical treatments, such that they are no longer capable of adherence to a target nucleic acid and blocking its action. It is also known that proteins, peptides, oligonucleotides, and the like have a very short lifetime (minutes to a few hours) in vivo, require effective delivery to the cell and, in some circumstances, directly to the nucleus in order to avoid degrading enzymes. Accordingly, these agents typically cannot be successfully delivered "naked", but need to be protected or formulated in a way that will allow their delivery in vivo.

The oligonucleotides of the present invention retain their biological activity by incorporation into microspheres. Additionally, the microspheres also provide high loading capabilities. In other words, larger doses of therapeutic nucleic acids can be administered to a subject by dosing with highly concentrated (e.g., 30-100% by weight nucleic acid) microspheres, based on the total weight of the microspheres. Unless otherwise specified herein, percentages are by weight, based on the total weight of the composition. The microspheres provide a non-viral delivery tool for antisense oligonucleotides and other types of nucleic acid molecules.

The microspheres are comprised of the biologically active compound in a substantially spherical form. Typically, the microspheres have a substantially narrow particle size distribution with an average particle size of not greater than 50 microns. Typically, the particle size will be less than 10 microns, more typically less than 5 microns. Preferably, they have a narrow size distribution with an average particle size on the order of between about 0.04 to about 8 microns, or between about 0.1 to about 4 microns, or between about 0.2 to about 4 microns, or between about 0.4 to about 4 microns, and, for applications wherein about 1 micron microspheres are desirable, about 1 micron to about 3 microns. An average particle size can be about 2 microns, for example, and the particle size range can be tailored to fit the desired application.

The microspheres are preferably comprised of nucleic acids which are substantially amorphous or non-crystalline, that is they are in an amorphous or semi-crystalline form. As used herein, "amorphous" refers to a generally random solid form of nucleic acid wherein crystalline lattices of the nucleic acid(s) within the microsphere are absent and "semi-crystalline" refers to a generally random solid form of nucleic acid wherein the nucleic acid content of the microsphere is comprised of less than 50% of crystalline lattice forms of the nucleic acid(s).

Delivering the biologically active compound in the microsphere form with the desired size can increase the efficacy of the drug and reduce waste. This may also reduce adverse effects caused by high dosage amounts of the active agent. The size of the microsphere can determine to what organ it is targeted. Additionally, optimal particle size control of microspheres for delivery of biological agents in vivo is important since only microspheres of particular size can be taken up by target cells. A larger size microsphere than described herein might trigger macrophages and other immune mechanisms to degrade the biological particle, while a smaller size might dissolve too quickly.

In making microspheres, the desired biological agent, typically an oligonucleotide or other nucleic acid compound, is dissolved in an aqueous solution. This is combined with water-soluble polymer(s) such as polyvinyl pyrrolidone (PVP) and polyethylene glycol (PEG) and combinations thereof. The water soluble polymers do not form a substantial part of the microspheres, if at all, but aid in the preparation of the microspheres. The nucleic acids can comprise up to 100 weight percent of the microsphere composition. Typically, they will comprise at least 20 weight percent, typically at least about 30 weight percent, preferably at least about 50 weight percent, more preferably at least 70 weight percent, and most preferably at least about 90 weight percent. The nucleic acids can comprise at least about 95 weight percent of the microspheres. In one aspect, the nucleic acids comprise between about 30 percent and about 100 percent of the microspheres. It is usually preferred to form microspheres in an aqueous/water-soluble polymer(s) mixture at a moderately acidic pH.

For example, often the polymer or polymers are dissolved in a buffer solution, such as sodium acetate, at a pH of about 5.3. Microspheres by this general technique can also be made with other polymers such as polysaccharides, including positively and negatively charged polysaccharides and other biocompatible polymers. The order of addition of the components may be altered to form microspheres with different chemical and physical properties such as size, morphology and/or surface charge.

The preferred water soluble polymers are water soluble or soluble in water miscible solvent. The water soluble polymers may be solubilized by first being dissolved in a water miscible solvent and then combining the polymer solution with an aqueous solvent.

In some microsphere preparations it is preferred to combine nucleic acids with a polycation prior to formation of the microsphere. Avoiding polycation use, however, can be advantageous in some instances because some cations can be associated with toxicity issues. The use of a polyanion, a polyanion cross-linking agent, or other cross-linking agent may also be employed for making these microspheres. Examples of preferred polycations are poly-lysine and poly-ornithine. Others include poly-ethylene-imine (PEI), prolamin, protamine, polyvinyl pyrrolidone (PVP), polyarginine, vinylamine, and combinations thereof.

When a polycation component is included in the preparation of the microspheres and also in the microspheres, it can be present at a level of from about 0 to about 80 weight percent of the total microsphere forming composition. Microspheres made with polycations can contain at least about 2 weight percent, or can contain at least about 5 weight percent, or can contain at least about 10 weight percent, or can contain at least about 20 weight percent, or can contain at least about 30 weight percent by weight of the polycation, with the balance, in general, comprising the nucleic acid.

When a polycation component is included in the preparation of the microspheres, it can be present at a level as high as 50 weight percent of the total composition. When present, a preferred range is between about 20 to about 40 weight percent polycation component, based on the total weight of the composition.

In some microsphere production applications, energy (such as in the form of heat or other energy sources) is supplied to the composition in order to facilitate microsphere formation. It has been discovered that energy addition can be useful for production of some types of microspheres of the present invention.

The microsphere compositions can contain multiple biologically active compounds. Thus, the microspheres, either individually or collectively as a group of microspheres, can contain more than one nucleic acid, e.g., one or more oligonucleotide. In addition, other molecules may be added to the surface of the nucleic acid microspheres after their formulation including but not limited to antibodies, receptor ligands or chemoattractants.

Although numerous techniques may be useful for the preparation of microspheres of the present invention (see references incorporated herein by reference), the following has been found particularly useful in the preparation of the microspheres of the present invention.

An aqueous solution of the nucleic acid mixture is prepared by comprising polycation at volumetric ratios of polycation: nucleic acid of from about 0.5:1 to about 4:1. Polymer solutions of polyvinyl pyrrolidone and/or of polyethylene glycol are prepared and combined with the nucleic acid-containing solution. Changing the temperature of the combined solution by heating or cooling or combinations thereof, and centrifuging and washing multiple times provide an aqueous condensed suspension which typically is frozen and lyophilized to form a dry powder of microspheres comprising the nucleotide(s) and polycation. The temperature of the mixture prior to formation of the microspheres can be lowered or raised from room temperature and at a rate of from about 0.1 to about 400° C./minute. For cooling applications, the mixture is typically cooled to from about 35 to about −196° C. And for heating applications, the mixture is heated to from about 4 to about 100° C.

Other excipients can be added to the final composition or the pre-microsphere forming mixture, such as polysaccharides, positively or negatively charged polysaccharides, and other polymers which preferably are biocompatible. The order of addition can be changed which may result in the formation of microspheres with different chemical and/or physical properties. Other moieties may be added to the surface to work as chemoattractants, or as receptor ligands, for example.

Microspheres according to the invention are useful, non-viral delivery vehicles for plasmid DNA, antisense oligonucleotides and other nucleic acid molecules.

The microsphere compositions can be in the form of liquid suspensions (preferably be aqueous), in dry powder form, in suspensions in organic solvents, or microencapsulated in solid form within other polymers.

As stated above, the present invention microspheres can be dosed through a variety of routes of administration. The actual dosing amount of active agent, concentration of the formulation and volume of the formulation to be dosed will be determined by skilled clinicians and will generally depend on a number of factors including, but not limited to, the disease or condition to be treated, age, sex and weight of the subject to be treated, potency of the nucleic acid for treating the particular target, concentration of the nucleic acid in the dosing formulation, and so on. As used herein, an "effective amount" refers to that amount of microspheres of the present invention that prevent, treat or ameliorate a disease or condition in a subject.

Microspheres according to the invention have an especially protective characteristic. In vitro studies using Beta-Galactosidase microspheres indicate the microsphere form shielded the DNA from nucleases. Often DNA and oligonucleotides are thioated with a view toward slowing degradation. For example, typically AS-oligonucleotides are in thioated form. Because of the protective features of the microspheres, the need for such thioated form can be lessened or not used at all.

A preferred method of the present invention is directed to the prevention or amelioration of autoimmune insulin-dependent diabetes by formulating and injecting antisense (AS)-oligonucleotide microspheres described herein that target the primary transcripts of CD40, CD80 and CD86. These oligonucleotides have been designed to induce immune tolerance in an attempt to prevent destruction of the insulin producing beta cells in the NOD mouse model. The events leading to the destruction of these beta cells is illustrated in FIG. 1. This illustrates how Type 1 diabetes is manifested by the autoimmune destruction of the pancreatic insulin-producing beta cells in the NOD mouse, as well as in humans. At the time of clinical onset of diabetes, humans maintain 10-20% of their residual beta cell mass. Sparing of this residual mass can result in maintenance of insulin levels which are adequate to regulate glucose levels. Preferred microspheres of the invention are provided to interfere with the autoimmune destruction of the beta cells that is illustrated in FIG. 1.

It will be appreciated that dendritic cells (DC) can be activated to be potent antigen presenting cells that are found in all tissues and that are highly concentrated under the skin. These antigen presenting dendritic cells function as triggers of the immune response through the activation of T-cells, particularly in lymph nodes.

Figure 2:
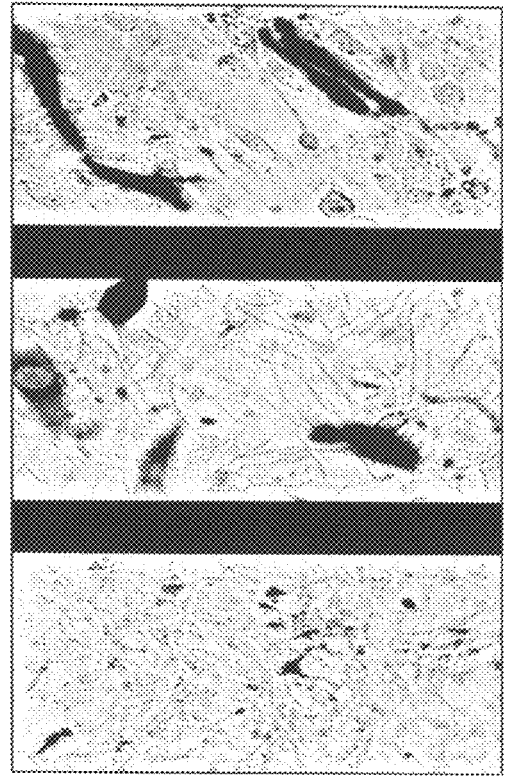
FIG. 2 is a diagram of the Beta-Galactosidase gene-containing plasmid DNA vector.
Figure 3:
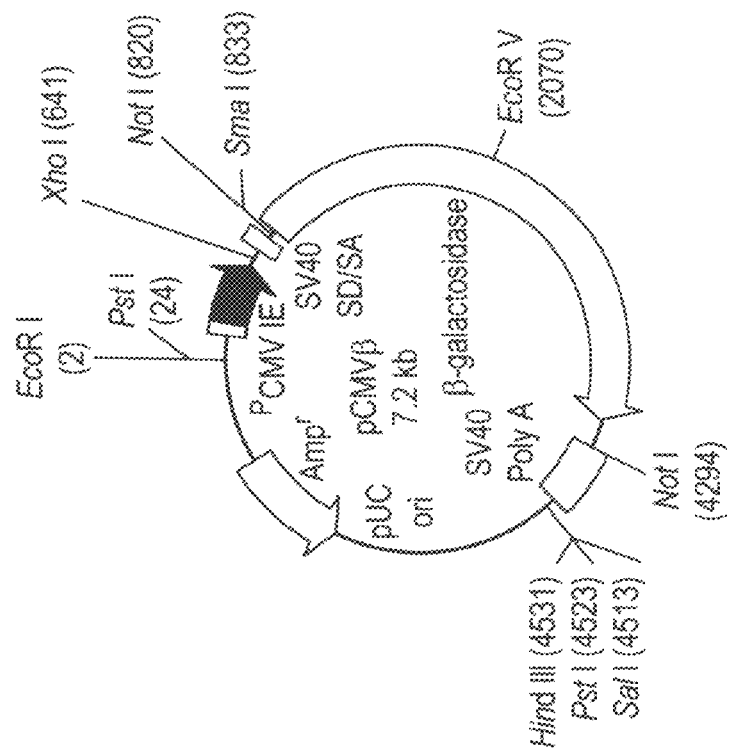
FIG. 3 shows photomicrographs providing evidence for transfection of NIH 3T3 fibroblast cells with the Beta-Galactosidase gene-containing plasmid DNA (pDNA) microspheres.

FIG. 2 is a drawing of a plasmid vector containing the Beta-galactosidase gene that can be used to transfect NIH 3T3 fibroblast cells. In vitro evidence for the transfection of NIH 3T3 fibroblast cells with the plasmid DNA microspheres is shown in FIG. 3 are the appearance of cells which stain blue in color in response to the addition of the Beta-Galactosidase X-gal substrate.

Figure 4:
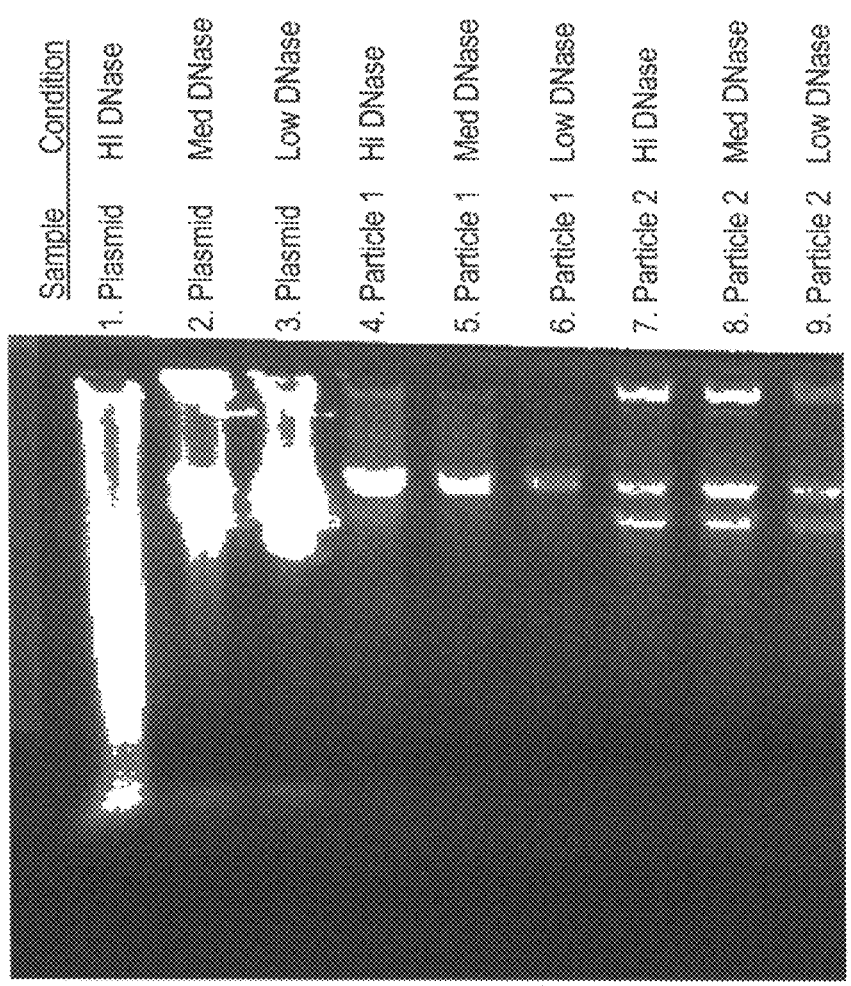
FIG. 4 is a photomicrograph of an agarose electrophoresis gel of naked pDNA and of two pDNA microsphere formulations according to the invention, each after exposure to DNAase.

FIG. 4 illustrates the ability of microspheres in vitro to protect DNA in solution. This is an agarose electrophoresis gel showing nuclease protection imparted by microspheres of plasmid DNA produced generally as noted herein. In the Plasmid samples 1, 2 and 3, naked plasmid DNA was exposed to DNAse, with the smears indicating plasmid DNA degradation at each of the three levels of DNAase exposure. In the Particle 1 and Particle 2 samples, plasmid DNA microsphere formulations were exposed to DNAase. The lack of smearing indicates the microsphere formulations show shielding of the plasmid DNA from degradation. Particle 1 plasmid DNA samples show enhanced protection over Particle 2 plasmid DNA samples.

Figure 5:
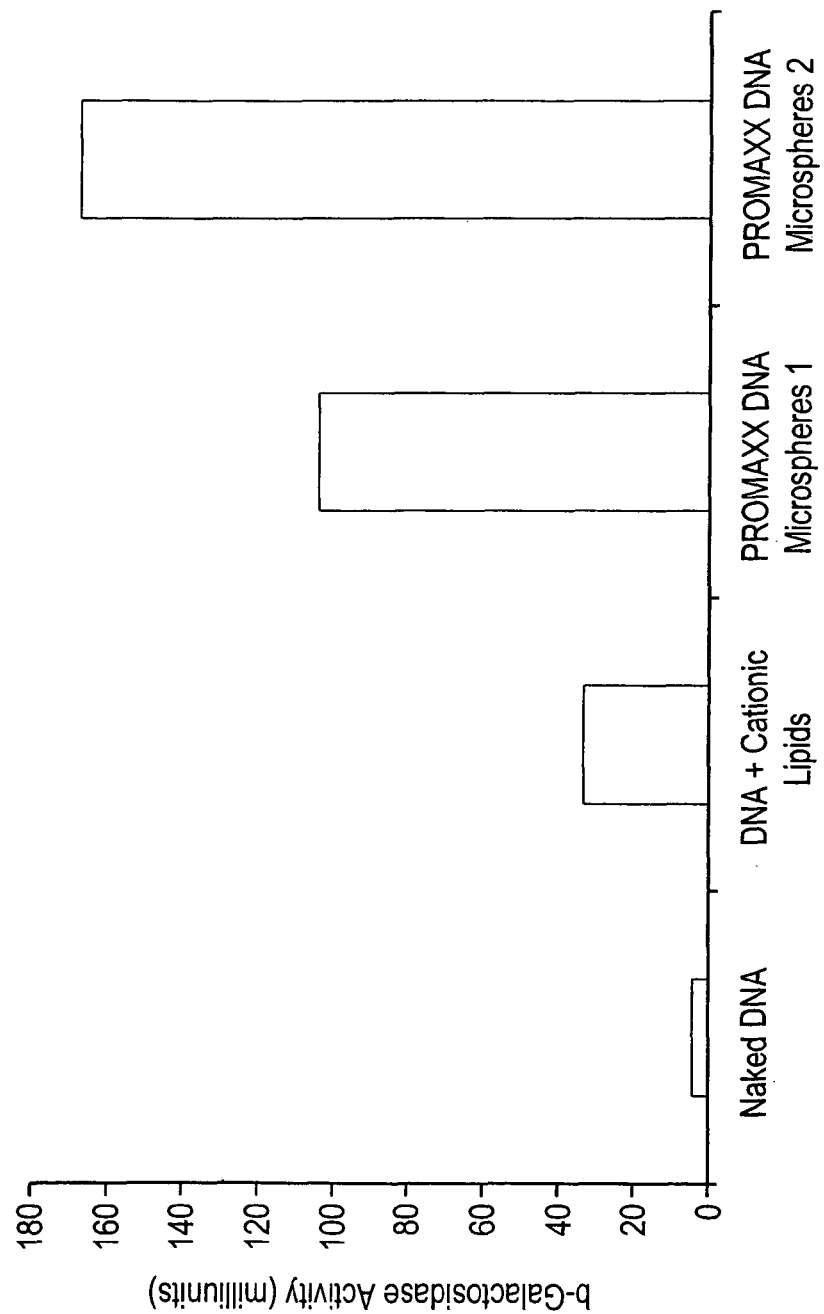
FIG. 5 is a bar graph of Beta-Galactosidase activity in four different plasmid DNA transfection applications.

FIG. 5 quantitates the levels of expression of transfected Beta-Galactosidase activity of four different plasmid DNA applications when transfected into cells. The naked plasmid DNA application showed very low levels. Somewhat greater levels are indicated for plasmid DNA-cationic lipid complex application using lipofectamine, a commercial cationic lipid, as the delivery vehicle. Substantially greater activity is shown for two pDNA microspheres, with Microspheres 1 corresponding to Particle 1 of FIG. 4, and Microspheres 2 corresponding to Particle 2 of FIG. 4.

The following Examples illustrate certain features and advantages of the invention in order to further illustrate the invention. The Examples are not to be considered limiting or otherwise restrictive of the invention.

EXAMPLE 1

Three AS-oligonucleotides targeted to the CD40, CD80 and CD86 primary transcripts were synthesized by the DNA synthesis facility at University of Pittsburgh (Pittsburgh, Pa.). The AS-oligonucleotides sequences, an asterisk indicating thioation, are:

```
CD       5'C*AC* AG*C C*GA* GG*C* AA*A     Seq ID 1
40-AS:
         GA*C* AC*C A*T*G C*AG* GG*C* A-3'

CD80-AS: 5'-G*GG* AA*A G*CC* AG*G A*AT* CT* Seq ID 2
         A G*AG* CC*A A*TG G*A-3'

CD86-AS: 5'-T*GG* GT*G C*TT* CC*G T*AA*    Seq ID 3
         GT*T C*TG* GA*A C*AC* G*T*C-3'
```

An aqueous solution of the oligonucleotide mixture was prepared by combining aliquots of three oligonucleotide solutions, each of which contained one type of oligonucleotide, to form a 10 mg/ml solution of the three types of oligonucleotides. Four batches of aqueous solution of oligonucleotides-mixture were prepared. 10 mg/ml poly-L-lysine-HBr in deionized water (poly-L-lysine-HBr up to 50,000 by Bachem, King of Prussia, Pa.) was prepared. Poly-L-lysine-HBr was added to the oligonucleotides solution at volumetric ratios of 1:1, 2:1, 3:1 and 4:1, as described in Table 1. Batches were labeled 1, 2, 3, and 4. The mixtures were vortexed gently. A 25% polymer solution containing 12.5% PVP (polyvinyl pyrrolidone, 40,000 Daltons, Spectrum Chemicals, Gardena, Calif.) and 12.5% PEG (polyethylene glycol, 3,350 Daltons, Spectrum Chemicals, Gardena, Calif.) in 1M Sodium Acetate (Spectrum, Gardena, Calif.) at pH 5.5 was made. The polymer solution was added to batches 1-4 in a 2:1 volumetric ratio as described in Table 1 showing AS-oligonucleotides, poly-L-lysine-HBr and PEG/PVP volumes in batches 1-4:

TABLE 1

| Batch | Oligonucleotide | Poly-L-lysine.HBr | 25% PEG/PVP | Total Volume |
|---|---|---|---|---|
| 1 | 750 µl | 0.75 ml | 3.0 ml | 4.50 ml |
| 2 | 750 µl | 1.50 ml | 4.5 ml | 6.75 ml |
| 3 | 750 µl | 2.25 ml | 6.0 ml | 9.00 ml |
| 4 | 750 µl | 3.00 ml | 7.5 ml | 11.25 ml |

The batches were incubated for 30 minutes at 70° C. and then cooled to 23° C. Upon cooling, the solution became turbid and precipitation occurred. The suspension was then centrifuged, and the excess PEG/PVP was removed. The resulting pellet was washed by resuspending the pellet in deionized water, centrifugation and removal of the supernatant. The washing process was repeated three times. The aqueous condensed suspension was frozen and lyophilized to form a dry powder of microspheres comprising oligonucleotide and poly-L-lysine.

Figure 6:
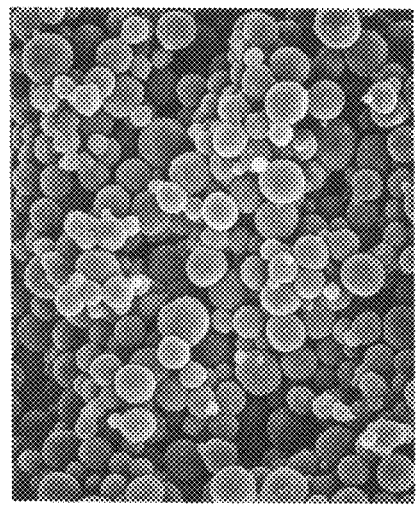
FIG. 6 through FIG. 9 are scanning electron migrographs of microspheres of AS-oligonucleotides and poly-L-lysine polycation.

FIG. 6 presents a scanning electron micrograph (SEM) of batch No. 1 (poly-L-lysine:oligonucleotide ratio of 1:1). Microspheres, 0.5-4 µm in size, with an average particle size of approximately 2.5 µm were fabricated. Precipitation of an unknown material was also observed. Additional studies by HPLC determined that the precipitation was comprised of residual PEG/PVP, mostly PVP.

Figure 7:
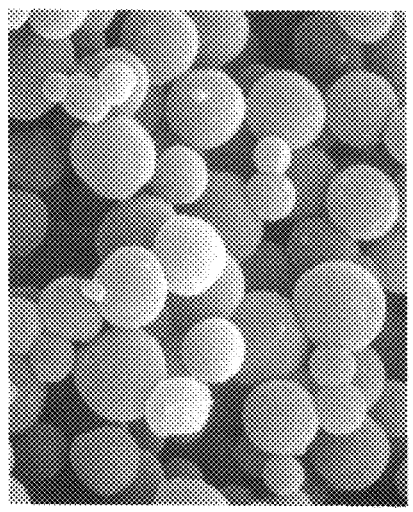

FIG. 7 presents an SEM of batch No. 2 (poly-L-lysine:oligonucleotide ratio of 2:1). Microspheres, 0.2-4 µm in size, with an average particle size of approximately 1 µm were fabricated.

Figure 8:
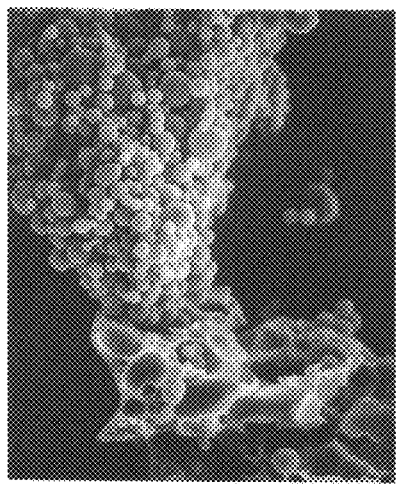

FIG. 8 presents an SEM of batch No. 3 (poly-L-lysine:oligonucleotide ratio of 3:1). Microspheres, 0.2-4 µm in size, with an average particle size of approximately 1 µm were fabricated. Precipitation of an unknown material was also observed. Additional studies by HPLC determined that the precipitation was comprised of residual PEG/PVP, mostly PVP.

Figure 9:
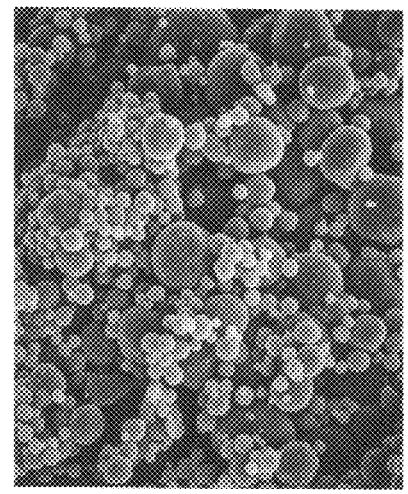

FIG. 9 presents an SEM of batch No. 4 (poly-L-lysine:oligonucleotide ratio 4:1). Microspheres, 0.2-6 microns in size were fabricated. There is polydispersity in sizes, where approximately half of the particles having an average particle size of 1 µm, and half of the particles having an average particle size of 5 µm.

EXAMPLE 2

AS-oligonucleotides targeted to the CD40, CD80 and CD86 primary transcripts were the AS-oligonucleotides sequences of Example 1. An aqueous solution of the oligonucleotides mixture was prepared by combining aliquots of three oligonucleotide solutions, each of which contained one type of oligonucleotide, to form a 10 mg/ml solution of the three types of oligonucleotides. Four batches of solutions of the oligonucleotides mixture were prepared. 5 mg/ml poly- L-ornithine-HBr in deionized water (poly-L-ornithine-HBr 11,900 (vis) by Sigma) solution was prepared.

Poly-L-ornithine-HBr was added to the oligonucleotides solution at varying volumetric ratios as described in Table 2. Batches were labeled 1, 2, 3, and 4. The mixtures were vortexed gently. A 25% polymer solution containing 12.5% PVP (40,000 Daltons, Spectrum Chemicals, Gardena, Calif.) and 12.5% PEG (3,350 Daltons, Spectrum Chemicals, Gardena, Calif.) in 0.1.M Sodium Acetate (Spectrum Chemicals, Gardena, Calif.) at pH=5.5 was made. The polymer solutions were added to batches 1-4 at the different volumetric ratios of Table 2. Incubation and rinses followed as described in Example 1. Table 2 provides AS-oligonucleotides, poly-L-ornithine-HBr, PEG/PVP and PEG volumes in batches 1-4.

TABLE 2

| Batch | Oligo-nucleotide | Poly-L-ornithine.HBr | 25% PEG/PVP | 25% PEG | Total Volume |
|---|---|---|---|---|---|
| 1 | 1.5 ml | 1.5 ml | 3 ml | — | 6.0 ml |
| 2 | 1.5 ml | 3.0 ml | 8 ml | — | 12.5 ml |
| 3 | 1.5 ml | 1.5 ml | — | 6 ml | 9.0 ml |
| 4 | 1.5 ml | 4.5 ml | — | 6 ml | 12.0 ml |

Figure 10:
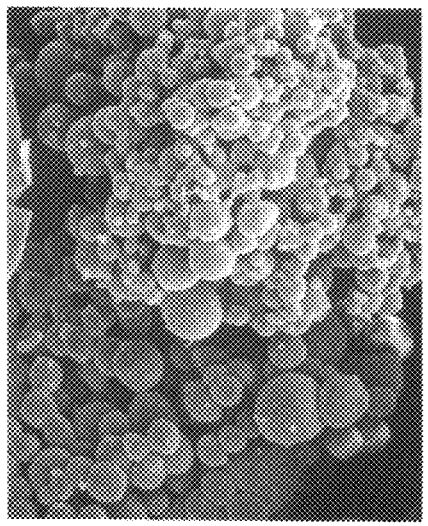
FIG. 10 through FIG. 13 are scanning electron micrographs of microspheres comprised of AS-oligonucleotides and poly-L-ornithine polycation.

FIG. 10 presents an SEM of batch No. 1 (poly-L-ornithine: oligonucleotide ratio of 1:1). Microspheres, 0.2-8 µm in size, with an average particle size of approximately 2 µm were fabricated. Precipitation of an unknown material was also observed. Additional HPLC studies were able to prove that this precipitation was comprised of residual PEG/PVP, mostly PVP.

Figure 11:
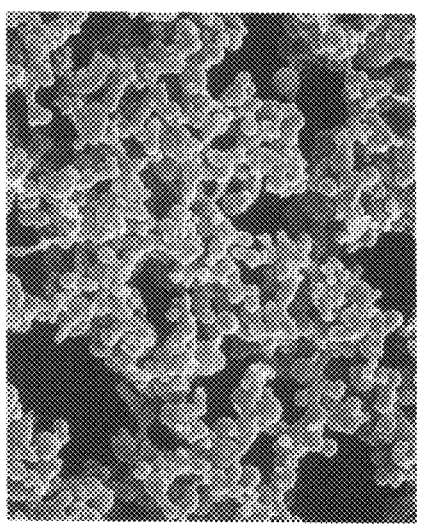

FIG. 11 presents an SEM of batch No. 2 (poly-L-ornithine: oligonucleotide ratio of 2:1). Microspheres, 0.2-8 µm in size, with an average particle size of approximately 2 µm were fabricated. Many of the microspheres were fused together. Precipitation of an undefined material was also observed. Additional HPLC studies were able to prove that this precipitation was comprised of residual PEG/PVP, mostly PVP.

Figure 12:
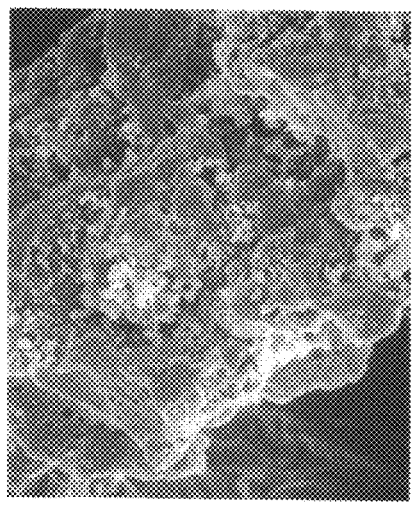

FIG. 12 presents an SEM of batch No. 3 (poly-L-ornithine: oligonucleotide ratio of 1:1, PEG only). A precipitate of amorphous shape was formed. This indicated that the presence of PVP in the formulation had an important role in the formation of micro spheres.

Figure 13:
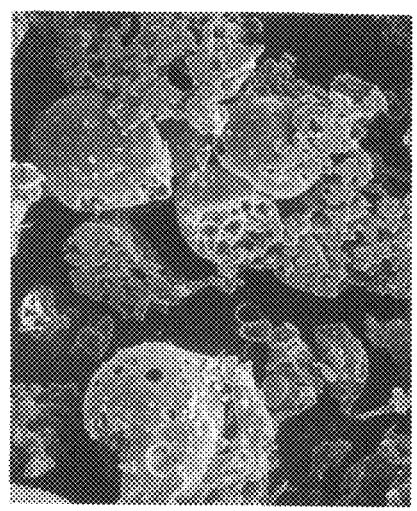

FIG. 13 presents an SEM of batch No. 4 (poly-L-ornithine: oligonucleotide ratio of 1:3, PEG only). Porous microspheres 10-50 µm in size, broken microspheres, and 2-10 µm chains of fused microspheres were formed. Single microspheres were not observed. This batch indicated that the presence of PVP in the formulation had an important role in the formation of microspheres.

EXAMPLE 3

Three AS-oligonucleotides targeted to the CD40, CD80 and CD86 primary transcripts were synthesized with the oligonucleotide sequences of Example 1. An aqueous solution of the oligonucleotides mixture was prepared by combining aliquots of three oligonucleotide solutions, each of which contained one type of oligonucleotide, to form a 10 mg/ml solution of the three types of oligonucleotides. Two batches of solution of oligonucleotide-mixture were prepared.

A 25% polymer solution containing 12.5% PVP (40,000 Daltons, Spectrum Chemicals, Gardena, Calif.) and 12.5% PEG (3,350 Daltons, Spectrum Chemicals, Gardena, Calif.) in 0.1M Sodium Acetate (Spectrum Chemicals, Gardena, Calif.) at pH 5.5 was made. Also 25% PEG in 0.1M Sodium Acetate at pH 5.5 was made. The polymer solutions were added to batches 1-2 at different volumetric ratios, as described in Table 3. Incubation and rinses followed as described in Example 1. Table 3 gives AS-oligonucleotides, PEG/PVP and PEG volumes in batches 1-2.

TABLE 3

| Batch | Oligonucleotide | 25% PEG/PVP | 25% PEG | Total Volume |
|---|---|---|---|---|
| 1 | 1.5 ml |  | 3.0 ml | 4.5 ml |
| 2 | 1.5 ml | 3.0 ml |  | 4.5 ml |

Figure 14:
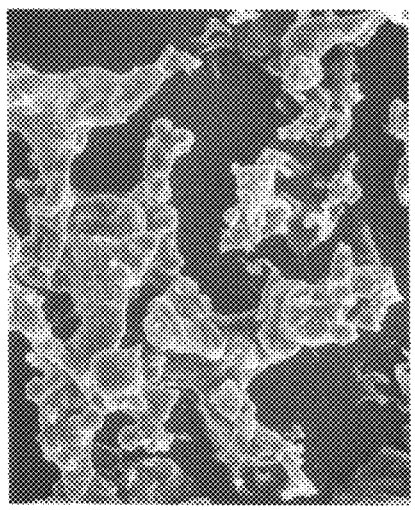
FIG. 14 and FIG. 15 are scanning electron micrographs of microspheres of AS-oligonucleotides formed without a polycation component.

FIG. 14 presents an SEM of batch 1 (PEG:oligonucleotide 2:1). A precipitate of amorphous shape was formed. This batch showed again that the presence of PVP played an important role in the formation of the microspheres.

Figure 15:
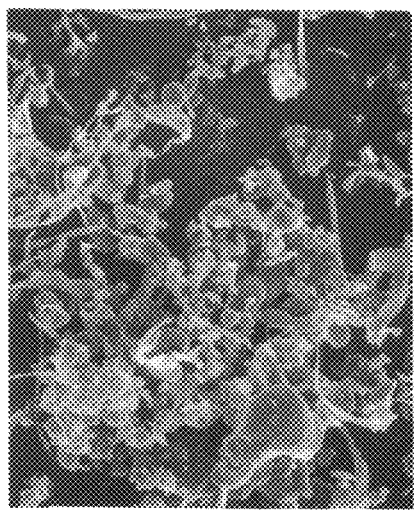

FIG. 15 presents an SEM of batch 2 (PEG/PVP:oligonucleotide 2:1). Microspheres with particle size distribution of 0.2-6 µm were fabricated, and long strips of unidentified source are seen as well. This batch showed that microspheres could be formed without polycation.

EXAMPLE 4

In vivo studies were conducted using the NOD mouse model of Type 1 diabetes mellitus. Type 1 diabetes is manifested by the autoimmune destruction of the pancreatic insulin-producing beta cells as illustrated in FIG. 1. AS-oligonucleotides were used in three applications in an attempt to interfere with the autoimmune destruction of beta cells. The goal was to interfere with the dendritic cell function by targeting the primary transcripts of CD40, CD80 and CD86, which encode dendritric cell surface proteins required for T-cell activation. Dendritic cells with low levels of CD40, CD80 and CD86 are known to promote suppressive immune cell networks in vivo. These cascades can result in T-cell hyporesponsiveness to beta cells in vivo.

In the first group of test animals, dendritic cells were propagated ex vivo from bone marrow progenitors of NOD mice. Combinations of the three AS-oligonucleotides targeting the primary transcripts of CD40, CD80 and CD86 were added to the cells in tissue culture. After incubation, the AS-oligonucleotide transfected dendritic cells were injected into syngenetic recipients of 5 to 8 weeks of age (not yet diabetic). This is an ex vivo delivery approach.

In parallel, AS-oligonucleotide microspheres were injected directly into other NOD mice of the same age. A single injection was carried out on each thus-treated mouse. Another group of these NOD mice was not treated and served as a control.

Figure 16:
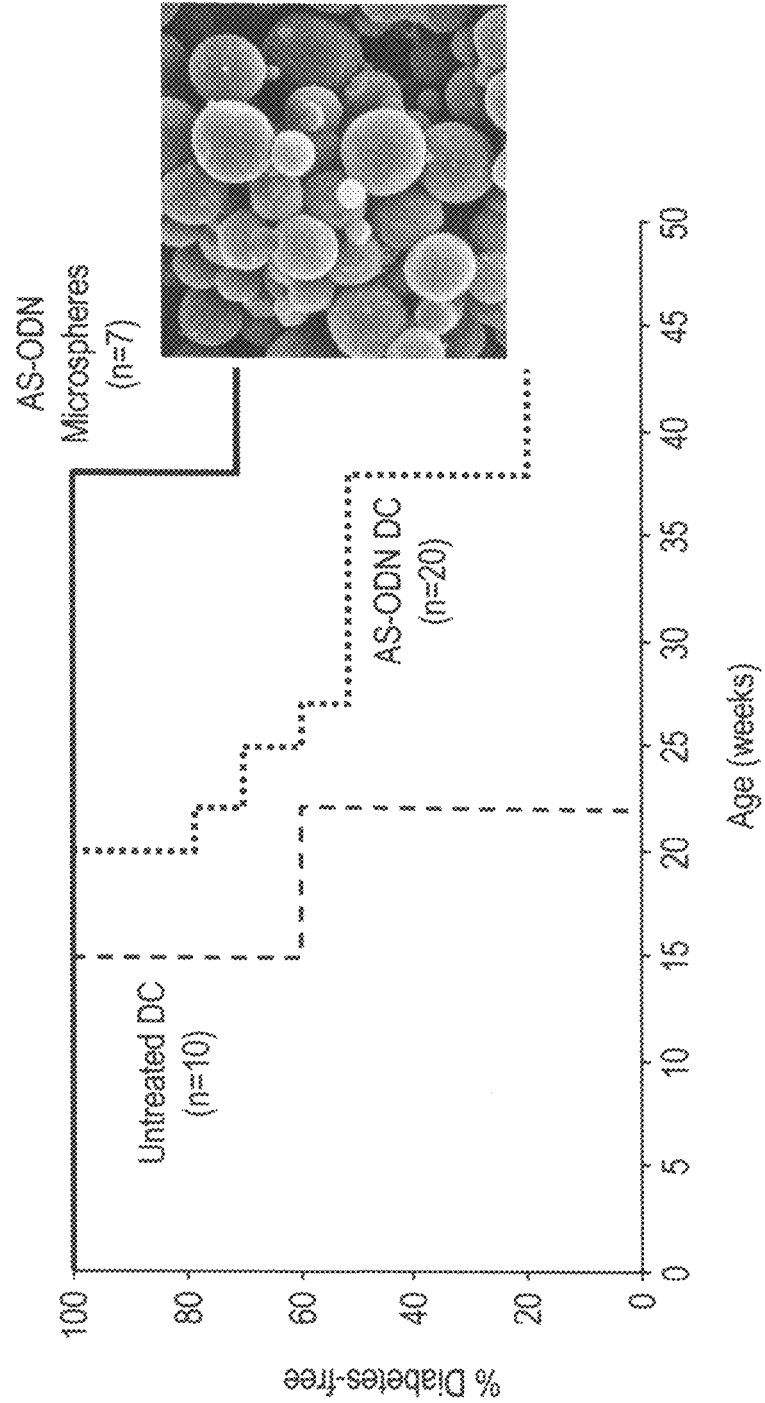
FIG. 16 is a plot summarizing diabetes incidence in three groups of NOD mice treated with microspheres of the present invention and according to other procedures for delivery of AS oligonucleotides targeting three primary transcripts.

FIG. 16 shows that the control, untreated NOD mice all developed diabetes by age 23 weeks. The group treated with ex vivo AS-oligonucleotide transfected and re-infused dendritic cells (AS-ODN DC) showed delayed development of diabetes, with 20% remaining "Diabetes Free", indicating glucose levels are maintained within a non-diabetic range. Of the NOD mice injected directly in vivo with microspheres, 71% remained "Diabetes Free" at 43 weeks.

EXAMPLE 5

A fluorescent Cy3 labeled short interfering RNA duplex, siGLO Cyclophilin B siRNA (Mouse), from Dharmacon (Lafayette, Colo.). The double-stranded RNA sequence is shown as Seq ID 4 and its complement, Seq ID 5:

```
Cyclophilin B 5'-GGAAAGACUGUUCCAAAAAUU-3'    Seq ID 4
siRNA

Complement    5'-UUUUUGGAACAGUCUUUCCUU-3'    Seq ID 5
```

An aqueous solution of the siRNA was prepared as a 15 mg/mL solution. Also, 15 mg/mL of Poly-L-lysine-HBr in deionized water (poly-L-lysine 30,000-70,00 MW, Sigma) was prepared. The Poly-L-lysine was added to the siRNA at a volumetric ratio of 1:1, as described in Table 1. The mixture was vortexed gently. A 25% polymer solution containing 12.5% PVP (polyvinyl pyrrolidone, 40,000 Daltons, Spectrum Chemicals, Gardena, Calif.) and a 12.5% PEG (polyethylene glycol, 3350 Daltons, Spectrum, Gardena, Calif.) in 1M Sodium acetate (Spectrum, Garden, Calif.) at pH 5.5 was made. The polymer solution was added to the siRNA/poly-L-lysine mixture in a 2:1 volumetric ratio as described in Table 4 showing siGLO siRNA duplex, poly-L-lysine-HBr and PEG/PVP volumes:

TABLE 4

| Batch | siGLO siRNA | Deionized water | Poly-L-lysine HBr | 25% PEG/PVP | Total Volume |
| --- | --- | --- | --- | --- | --- |
| 1 | 0.5 mL | 0.25 mL | 0.5 Ml | 2.5 mL | 3.75 mL |

The batch was incubated for 30 minutes at 58 C, and then cooled to on ice for 30 minutes. Upon cooling the solution became turbid and precipitation occurred. The suspension was then centrifuged, and the excess PEG/PVP was removed. The resulting pellet was washed by resuspending the pellet in deionized water, centrifugation and removal of supernatant. The washing process was repeated three times. The aqueous condensed suspension was frozen at −80 C and lyophilized to form a dry powder of microspheres comprised of Cy3 labeled siGLO Cyclophilin B siRNA duplex and poly-L-lysine.

Figure 17:
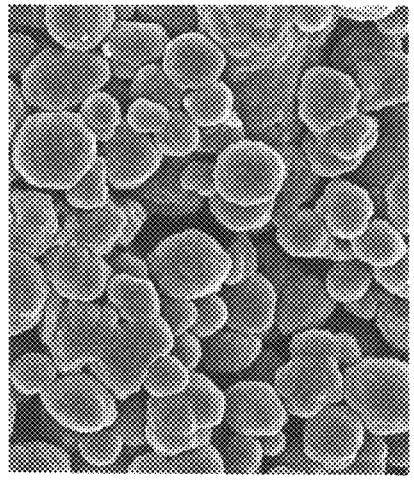
FIG. 17 is a scanning electron micrograph (SEM) of siRNA microspheres according to the invention.

FIG. 17 presents a scanning electron micrograph (SEM) of a batch of the microspheres (poly-L-lysine:siRNA duplex ratio of 1:1). Microspheres, 0.2-1.4 microns in size, with an average particle size of 0.48 microns were thus fabricated.

It will be understood that the embodiments of the present invention which have been described are illustrative of some of the applications of the principles of the present invention. Numerous modifications may be made by those skilled in the art without departing from the true spirit and scope of the invention. Various features which are described herein can be used in any combination and are not limited to precise combinations which are specifically outlined herein.

The invention claimed is:

1. An aqueous process for producing biologically active microspheres comprising nucleic acids, the process comprising (a) dissolving the nucleic acids with an aqueous solvent to form an aqueous composition, wherein at least one water soluble polymer is added to the aqueous solvent, and (b) forming microspheres comprising nucleic acids, said microspheres having an average particle size of not greater than about 50 microns and being substantially free of said polymer.

2. The process according to claim 1, wherein at least one polycation is added to said solvent.

3. The process according to claim 2, wherein said polycation is poly-lysine.

4. The process according to claim 3, wherein said polycation is poly-ornithine.

5. The process according to claim 1, wherein said nucleic acids are a first polyanion and wherein at least a second polyanion is added to said solvent.

6. The process according to claim 1, wherein said polymer is polyethylene glycol and polyvinyl pyrollidone.

7. The process according to claim 1, wherein said forming is carried out with the addition of a crosslinking agent to the composition.

8. The process according to claim 1, wherein said dissolving is carried out with the addition of energy to the composition.

9. An aqueous process for producing biologically active microspheres comprising nucleic acids, the process comprising dissolving the nucleic acids with an aqueous solvent to form a composition, wherein at least one water soluble polymer is added to the aqueous solvent, and forming nucleic acid microspheres from said composition, said microspheres having an average particle size of not greater than about 50 microns and substantially free of polymer, wherein said forming is carried out in the absence of a polycation component in said composition.

10. The process according to claim 1, wherein said forming is carried out in the absence of a cross-linking component in said composition.

11. The process according to claim 1, wherein said nucleic acids are a first polyanion and wherein said forming is carried out in the absence of a second polyanion component in said composition.

12. The process according to claim 1, wherein said forming is carried out in the absence of applying an energy source to form said microspheres from said composition.

13. The process according to claim 9 wherein said forming is carried out in the absence of a cross-linking component in said composition.

14. The process according to claim 9, wherein said nucleic acids are a first polyanion and said forming is carried out in the absence of a second polyanion component in said composition.

15. The process according to claim 9, wherein said forming is carried out in the absence of applying an energy source to form said microspheres from said composition.

16. The process according to claim 1, wherein the nucleic acids in the microspheres are less susceptible to nuclease degradation than the nucleic acids dissolved in the solvent.

17. The process according to claim 9, wherein the nucleic acids in the microspheres are less susceptible to nuclease degradation than the nucleic acids dissolved in the solvent.

18. The process of claim 1, wherein said dissolving in step (a) is carried out with the addition of heat and said forming in step (b) is carried out by cooling the composition.

19. The process according to claim 18, wherein said composition is cooled to from about 35° C. to about −196° C.

20. The process according to claim 18, wherein said composition remains a suspension as said cooling step is carried out.

21. The process according to claim 18, wherein the cooling is carried out at a rate of from about 0.1° C. to about 400° C. per minute.

22. The process according to claim 18, wherein the cooling provides a turbidity in the composition, wherein the turbidity comprises the microspheres.

23. The process according to claim 1 wherein, wherein said average particle size of the microspheres is between 0.04 and 10 microns.

24. The process according to claim 1 wherein, wherein said average particle size of the microspheres is between 0.04 and 5 microns.

25. The process according to claim 1, wherein said average particle size of the microspheres is between about 0.04 and about 8 microns.

26. The process according to claim 1, wherein said average particle size of the microspheres is between about 0.1 and about 4 microns.

27. The process according to claim 1, wherein said average particle size of the microspheres is between about 0.2 and about 4 microns.

28. The process according to claim 1, wherein said average particle size of the microspheres is between about 1 and about 3 microns.

29. The process according to claim 1, wherein nucleic acids comprise up to about 100 weight percent of the microspheres formed by the process.

30. The process according to claim 1, wherein nucleic acids comprise approximately 100 weight percent of the microspheres formed by the process.

31. The process according to claim 1, wherein nucleic acids comprise at least 20 weight percent of the microspheres formed by the process.

32. The process according to claim 1, wherein nucleic acids comprise at least 30 weight percent of the microspheres formed by the process.

33. The process according to claim 1, wherein nucleic acids comprise at least 50 weight percent of the microspheres formed by the process.

34. The process according to claim 1, wherein nucleic acids comprise at least 70 weight percent of the microspheres formed by the process.

35. The process according to claim 1, wherein nucleic acids comprise at least 90 weight percent of the microspheres formed by the process.

36. The process according to claim 1, wherein nucleic acids comprise at least 95 weight percent of the microspheres formed by the process.

37. The process according to claim 1, wherein nucleic acids comprise between about 30 and about 100 weight percent of the microspheres formed by the process.

38. The process of claim 1, wherein after said forming the microspheres are washed, yielding an aqueous suspension of microspheres.

39. The process according to claim 1, wherein after said forming the microspheres are washed and then dried to yield a dry powder.

40. The process according to claim 1, wherein the composition further comprises multiple biologically active agents, yielding microspheres comprised of multiple bioactive agents.

41. The process according to claim 1, wherein the composition further comprises a buffer.

42. The process according to claim 1, wherein the nucleic acids are thiolated.

43. The process according to claim 1, wherein the microspheres precipitate from an aqueous solution.

44. The process according to claim 1, wherein the microspheres are comprised of amorphous or semi-crystalline nucleic acids.

45. The process of claim 1, wherein step (a) is carried out at a temperature of from about 4° C. to about 100° C.

46. The process according to claim 2, wherein said polymer is polyethylene glycol and polyvinyl pyrollidone.

47. The process according to claim 2, wherein said forming is carried out with the addition of a crosslinking agent to the composition.

48. The process of claim 2, wherein said dissolving in step (a) is carried out with the addition of heat and said forming in step (b) is carried out by cooling the composition.

49. The process of claim 48, wherein step (b) comprises cooling the composition to a temperature of from about 35° C. to about −196° C.

50. The process of claim 2, wherein step (a) is carried out at a temperature of from about 4° C. to about 100° C.

51. The process according to claim 2, wherein step (a) comprises (i) adding at least one polycation and said nucleic acid to said solvent to form a solution, and (ii) adding water-soluble polymer to the solution of step (a).

52. The process of claim 51, wherein step (a) is carried out at a temperature of from about 4° C. to about 100° C.

53. The process according to claim 2 wherein, wherein said average particle size of the microspheres is between 0.04 and 10 microns.

54. The process according to claim 52 wherein, wherein said average particle size of the microspheres is between 0.04 and 5 microns.

55. The process according to claim 2, wherein said average particle size of the microspheres is between about 0.04 and about 8 microns.

56. The process according to claim 2, wherein said average particle size of the microspheres is between about 0.1 and about 4 microns.

57. The process according to claim 2, wherein said average particle size of the microspheres is between about 0.2 and about 4 microns.

58. The process according to claim 2, wherein said average particle size of the microspheres is between about 1 and about 3 microns.

59. The process according to claim 2, wherein nucleic acids comprise at least 20 weight percent of the microspheres formed by the process.

60. The process according to claim 2, wherein nucleic acids comprise at least 30 weight percent of the microspheres formed by the process.

61. The process according to claim 2, wherein nucleic acids comprise at least 50 weight percent of the microspheres formed by the process.

62. The process according to claim 2, wherein nucleic acids comprise at least 70 weight percent of the microspheres formed by the process.

63. The process according to claim 2, wherein nucleic acids comprise at least 90 weight percent of the microspheres formed by the process.

64. The process according to claim 2, wherein nucleic acids comprise a least 95 weight percent of the microspheres formed by the process.

65. The process according to claim 2, wherein nucleic acids comprise between about 30 and about 100 weight percent of the microspheres formed by the process.

66. The process of claim 2, wherein after said forming the microspheres are washed, yielding an aqueous suspension of microspheres.

67. The process according to claim 2, wherein after said forming the microspheres are washed and then dried to yield a dry powder.

68. The process according to claim 2, wherein the composition further comprises multiple biologically active agents, yielding microspheres comprised of multiple bioactive agents.

69. The process according to claim 2, wherein the composition further comprises a buffer.

70. The process according to claim 2, wherein the nucleic acids are thiolated.

71. The process according to claim 2, wherein the microspheres precipitate from an aqueous solution.

72. The process according to claim 2, wherein the microspheres are comprised of amorphous or semi-crystalline nucleic acids.

73. The process according to claim 2, wherein the volumetric ratio of polycation:nucleic acid in the composition is from about 0.5:1 to about 4:1.

\* \* \* \* \*